(12) United States Patent
Marui et al.

(10) Patent No.: US 8,835,177 B2
(45) Date of Patent: Sep. 16, 2014

(54) METHOD FOR TRANSFER OF GENE INTO FAT CELL OR PROGENITOR FAT CELL

(75) Inventors: Takahiro Marui, Shiga (JP); Tatsuji Enoki, Shiga (JP); Hiroaki Sagawa, Shiga (JP); Ikunoshin Kato, Shiga (JP)

(73) Assignee: Takara Bio Inc., Shiga (JP)

( * ) Notice: Subject to any disclaimer, the term of this patent is extended or adjusted under 35 U.S.C. 154(b) by 1088 days.

(21) Appl. No.: 11/917,853

(22) PCT Filed: Jun. 12, 2006

(86) PCT No.: PCT/JP2006/311754
§ 371 (c)(1),
(2), (4) Date: Dec. 17, 2007

(87) PCT Pub. No.: WO2006/134871
PCT Pub. Date: Dec. 21, 2006

(65) Prior Publication Data
US 2009/0162936 A1   Jun. 25, 2009

(30) Foreign Application Priority Data

Jun. 15, 2005  (JP) ................................ 2005-175690
Mar. 10, 2006  (JP) ................................ 2006-065710

(51) Int. Cl.
*C12N 15/87*   (2006.01)
*C07K 14/78*   (2006.01)
*C12N 15/86*   (2006.01)
*C12N 15/867*  (2006.01)

(52) U.S. Cl.
CPC ............. *C12N 15/86* (2013.01); *C07K 14/78* (2013.01); *C12N 2740/13045* (2013.01); *C12N 2810/857* (2013.01); *C12N 2533/52* (2013.01)
USPC .......................................... 435/455; 435/456

(58) Field of Classification Search
None
See application file for complete search history.

(56) References Cited

U.S. PATENT DOCUMENTS

2006/0121008 A1   6/2006   Ito et al.

FOREIGN PATENT DOCUMENTS

| EP | 1 094 114 A | 4/2001 |
| EP | 1 094 114 A1 | 4/2001 |
| EP | 1 541 674 A | 6/2005 |
| EP | 0 870 839 B1 | 5/2006 |
| WO | 95/26200 A1 | 10/1995 |
| WO | 97/18318 A1 | 5/1997 |
| WO | 00/01836 A1 | 1/2000 |
| WO | 03/106663 A1 | 12/2003 |

OTHER PUBLICATIONS

Kawaguchi et al "ADAM12 induces actin cytoskeleton and extracellular matrix reorganization during early adipocyte differentiation by regulating beta 1 integrin function" Journal of Cell Science; vol. 116, 2003, pp. 3893-3904.*
PCT Notification of Transmittal of Translation of the International Preliminary Report on Patentability dated Jan. 3, 2008.
H. Hanenberg et al., "Colocalization of retrovirus and target cells on specific fibronectin fragments increases genetic transduction of mammalian cells", Nature Medicine, vol. 2, No. 8, pp. 876-882, Aug. 1996.
S. Kamiya et al., "Fibronectin Peptides Derived from Two Distinct Regions Stimulate Adipocyte Differentiation by Preventing Fibronectin Matrix Assembly", Biochemistry, vol. 41, pp. 3270-3277, 2002.
C. S. Manno et al., "AAV-mediated factor IX gene transfer to skeletal muscle in patients with severe hemophilia B", Blood, vol. 101, No. 8, pp. 2963-2972, Apr. 15, 2003.
Japanese Office Action issued in corresponding Japanese Patent Application No. 2007-521277, Issued Aug. 23, 2011, and English translation of related parts thereof.
Summons to attend oral proceedings pursuant to Rule 115(1) EPC Communication issued on Jun. 28, 2012, in corresponding European Patent Application No. 06757239.6.
Office Action issued in corresponding Chinese Patent Application No. 2006-80021369.4, mailed May 31, 2012, and English translation thereof.
Decision to refuse a European patent application issued on Nov. 2, 2012, in corresponding European Patent Application No. 06757239.6.
Office Action issued in corresponding Chinese Patent Application No. 2006-80021369.4, mailed Jan. 31, 2012, and English translation thereof (as embedded in the partial reporting letter).

* cited by examiner

*Primary Examiner* — Catherine Hibbert
(74) *Attorney, Agent, or Firm* — Browdy and Neimark, PLLC

(57) ABSTRACT

A method for transferring a gene into a fat cell or progenitor fat cell comprising the step of infecting the fat cell or progenitor cell with a retrovirus vector having a foreign gene in the presence of a substance having both of a retrovirus-binding site and a target cell-binding site in the molecule or a mixture of a substance having a retrovirus-binding site and a substance having a target cell-binding site, the target cell-binding site having a region that can bind to VLA-5 and/or a region that can bind to VLA-4.

4 Claims, No Drawings

SEQUENCE LISTING

```
<160> NUMBER OF SEQ ID NOS: 6

<210> SEQ ID NO 1
<211> LENGTH: 271
<212> TYPE: PRT
<213> ORGANISM: Homo sapiens

<400> SEQUENCE: 1

Ala Ile Pro Ala Pro Thr Asp Leu Lys Phe Thr Gln Val Thr Pro
  1               5                  10                  15

Thr Ser Leu Ser Ala Gln Trp Thr Pro Pro Asn Val Gln Leu Thr
                 20                  25                  30

Gly Tyr Arg Val Arg Val Thr Pro Lys Glu Lys Thr Gly Pro Met
                 35                  40                  45

Lys Glu Ile Asn Leu Ala Pro Asp Ser Ser Ser Val Val Val Ser
                 50                  55                  60

Gly Leu Met Val Ala Thr Lys Tyr Glu Val Ser Val Tyr Ala Leu
                 65                  70                  75

Lys Asp Thr Leu Thr Ser Arg Pro Ala Gln Gly Val Val Thr Thr
                 80                  85                  90

Leu Glu Asn Val Ser Pro Pro Arg Arg Ala Arg Val Thr Asp Ala
                 95                 100                 105
```

```
Thr Glu Thr Thr Ile Thr Ile Ser Trp Arg Thr Lys Thr Glu Thr
            110                 115                 120

Ile Thr Gly Phe Gln Val Asp Ala Val Pro Ala Asn Gly Gln Thr
            125                 130                 135

Pro Ile Gln Arg Thr Ile Lys Pro Asp Val Arg Ser Tyr Thr Ile
            140                 145                 150

Thr Gly Leu Gln Pro Gly Thr Asp Tyr Lys Ile Tyr Leu Tyr Thr
            155                 160                 165

Leu Asn Asp Asn Ala Arg Ser Ser Pro Val Val Ile Asp Ala Ser
            170                 175                 180

Thr Ala Ile Asp Ala Pro Ser Asn Leu Arg Phe Leu Ala Thr Thr
            185                 190                 195

Pro Asn Ser Leu Leu Val Ser Trp Gln Pro Pro Arg Ala Arg Ile
            200                 205                 210

Thr Gly Tyr Ile Ile Lys Tyr Glu Lys Pro Gly Ser Pro Pro Arg
            215                 220                 225

Glu Val Val Pro Arg Pro Arg Pro Gly Val Thr Glu Ala Thr Ile
            230                 235                 240

Thr Gly Leu Glu Pro Gly Thr Glu Tyr Thr Ile Tyr Val Ile Ala
            245                 250                 255

Leu Lys Asn Asn Gln Lys Ser Glu Pro Leu Ile Gly Arg Lys Lys
            260                 265                 270

Thr

<210> SEQ ID NO 2
<211> LENGTH: 274
<212> TYPE: PRT
<213> ORGANISM: Homo sapiens

<400> SEQUENCE: 2

Pro Thr Asp Leu Arg Phe Thr Asn Ile Gly Pro Asp Thr Met Arg
  1               5                  10                  15

Val Thr Trp Ala Pro Pro Ser Ile Asp Leu Thr Asn Phe Leu
             20                  25                  30

Val Arg Tyr Ser Pro Val Lys Asn Glu Glu Asp Val Ala Glu Leu
             35                  40                  45

Ser Ile Ser Pro Ser Asp Asn Ala Val Val Leu Thr Asn Leu Leu
             50                  55                  60

Pro Gly Thr Glu Tyr Val Val Ser Val Ser Ser Val Tyr Glu Gln
             65                  70                  75

His Glu Ser Thr Pro Leu Arg Gly Arg Gln Lys Thr Gly Leu Asp
             80                  85                  90

Ser Pro Thr Gly Ile Asp Phe Ser Asp Ile Thr Ala Asn Ser Phe
             95                 100                 105

Thr Val His Trp Ile Ala Pro Arg Ala Thr Ile Thr Gly Tyr Arg
            110                 115                 120

Ile Arg His His Pro Glu His Phe Ser Gly Arg Pro Arg Glu Asp
            125                 130                 135

Arg Val Pro His Ser Arg Asn Ser Ile Thr Leu Thr Asn Leu Thr
            140                 145                 150

Pro Gly Thr Glu Tyr Val Val Ser Ile Val Ala Leu Asn Gly Arg
            155                 160                 165

Glu Glu Ser Pro Leu Leu Ile Gly Gln Gln Ser Thr Val Ser Asp
            170                 175                 180
```

```
Val Pro Arg Asp Leu Glu Val Ala Ala Thr Pro Thr Ser Leu
            185                 190                 195

Leu Ile Ser Trp Asp Ala Pro Ala Val Thr Val Arg Tyr Tyr Arg
            200                 205                 210

Ile Thr Tyr Gly Glu Thr Gly Gly Asn Ser Pro Val Gln Glu Phe
            215                 220                 225

Thr Val Pro Gly Ser Lys Ser Thr Ala Thr Ile Ser Gly Leu Lys
            230                 235                 240

Pro Gly Val Asp Tyr Thr Ile Thr Val Tyr Ala Val Thr Gly Arg
            245                 250                 255

Gly Asp Ser Pro Ala Ser Ser Lys Pro Ile Ser Ile Asn Tyr Arg
            260                 265                 270

Thr Glu Ile Asp

<210> SEQ ID NO 3
<211> LENGTH: 25
<212> TYPE: PRT
<213> ORGANISM: Homo sapiens

<400> SEQUENCE: 3

Asp Glu Leu Pro Gln Leu Val Thr Leu Pro His Pro Asn Leu His
 1               5                  10                  15

Gly Pro Glu Ile Leu Asp Val Pro Ser Thr
            20                  25

<210> SEQ ID NO 4
<211> LENGTH: 574
<212> TYPE: PRT
<213> ORGANISM: Artificial
<220> FEATURE:
<223> OTHER INFORMATION: Polypeptide having heparin-binding domain and
      cell-binding domains of fibronectin.

<400> SEQUENCE: 4

Pro Thr Asp Leu Arg Phe Thr Asn Ile Gly Pro Asp Thr Met Arg
 1               5                  10                  15

Val Thr Trp Ala Pro Pro Ser Ile Asp Leu Thr Asn Phe Leu
            20                  25                  30

Val Arg Tyr Ser Pro Val Lys Asn Glu Glu Asp Val Ala Glu Leu
            35                  40                  45

Ser Ile Ser Pro Ser Asp Asn Ala Val Val Leu Thr Asn Leu Leu
            50                  55                  60

Pro Gly Thr Glu Tyr Val Val Ser Val Ser Ser Val Tyr Glu Gln
            65                  70                  75

His Glu Ser Thr Pro Leu Arg Gly Arg Gln Lys Thr Gly Leu Asp
            80                  85                  90

Ser Pro Thr Gly Ile Asp Phe Ser Asp Ile Thr Ala Asn Ser Phe
            95                  100                 105

Thr Val His Trp Ile Ala Pro Arg Ala Thr Ile Thr Gly Tyr Arg
            110                 115                 120

Ile Arg His His Pro Glu His Phe Ser Gly Arg Pro Arg Glu Asp
            125                 130                 135

Arg Val Pro His Ser Arg Asn Ser Ile Thr Leu Thr Asn Leu Thr
            140                 145                 150

Pro Gly Thr Glu Tyr Val Val Ser Ile Val Ala Leu Asn Gly Arg
            155                 160                 165
```

```
Glu Glu Ser Pro Leu Leu Ile Gly Gln Gln Ser Thr Val Ser Asp
                170                 175                 180
Val Pro Arg Asp Leu Glu Val Val Ala Ala Thr Pro Thr Ser Leu
            185                 190                 195
Leu Ile Ser Trp Asp Ala Pro Ala Val Thr Val Arg Tyr Tyr Arg
        200                 205                 210
Ile Thr Tyr Gly Glu Thr Gly Gly Asn Ser Pro Val Gln Glu Phe
    215                 220                 225
Thr Val Pro Gly Ser Lys Ser Thr Ala Thr Ile Ser Gly Leu Lys
230                 235                 240
Pro Gly Val Asp Tyr Thr Ile Thr Val Tyr Ala Val Thr Gly Arg
                245                 250                 255
Gly Asp Ser Pro Ala Ser Ser Lys Pro Ile Ser Ile Asn Tyr Arg
            260                 265                 270
Thr Glu Ile Asp Lys Pro Ser Met Ala Ile Pro Ala Pro Thr Asp
        275                 280                 285
Leu Lys Phe Thr Gln Val Thr Pro Thr Ser Leu Ser Ala Gln Trp
    290                 295                 300
Thr Pro Pro Asn Val Gln Leu Thr Gly Tyr Arg Val Arg Val Thr
305                 310                 315
Pro Lys Glu Lys Thr Gly Pro Met Lys Glu Ile Asn Leu Ala Pro
                320                 325                 330
Asp Ser Ser Ser Val Val Ser Gly Leu Met Val Ala Thr Lys
            335                 340                 345
Tyr Glu Val Ser Val Tyr Ala Leu Lys Asp Thr Leu Thr Ser Arg
        350                 355                 360
Pro Ala Gln Gly Val Val Thr Thr Leu Glu Asn Val Ser Pro Pro
    365                 370                 375
Arg Arg Ala Arg Val Thr Asp Ala Thr Glu Thr Thr Ile Thr Ile
380                 385                 390
Ser Trp Arg Thr Lys Thr Glu Thr Ile Thr Gly Phe Gln Val Asp
                395                 400                 405
Ala Val Pro Ala Asn Gly Gln Thr Pro Ile Gln Arg Thr Ile Lys
            410                 415                 420
Pro Asp Val Arg Ser Tyr Thr Ile Thr Gly Leu Gln Pro Gly Thr
        425                 430                 435
Asp Tyr Lys Ile Tyr Leu Tyr Thr Leu Asn Asp Asn Ala Arg Ser
    440                 445                 450
Ser Pro Val Val Ile Asp Ala Ser Thr Ala Ile Asp Ala Pro Ser
455                 460                 465
Asn Leu Arg Phe Leu Ala Thr Thr Pro Asn Ser Leu Leu Val Ser
                470                 475                 480
Trp Gln Pro Pro Arg Ala Arg Ile Thr Gly Tyr Ile Ile Lys Tyr
            485                 490                 495
Glu Lys Pro Gly Ser Pro Pro Arg Glu Val Val Pro Arg Pro Arg
        500                 505                 510
Pro Gly Val Thr Glu Ala Thr Ile Thr Gly Leu Glu Pro Gly Thr
    515                 520                 525
Glu Tyr Thr Ile Tyr Val Ile Ala Leu Lys Asn Asn Gln Lys Ser
530                 535                 540
Glu Pro Leu Ile Gly Arg Lys Lys Thr Asp Glu Leu Pro Gln Leu
                545                 550                 555
Val Thr Leu Pro His Pro Asn Leu His Gly Pro Glu Ile Leu Asp
```

<210> SEQ ID NO 5
<211> LENGTH: 296
<212> TYPE: PRT
<213> ORGANISM: Homo sapiens

<400> SEQUENCE: 5

```
Ala Ile Pro Ala Pro Thr Asp Leu Lys Phe Thr Gln Val Thr Pro
  1               5                  10                  15
Thr Ser Leu Ser Ala Gln Trp Thr Pro Pro Asn Val Gln Leu Thr
                 20                  25                  30
Gly Tyr Arg Val Arg Val Thr Pro Lys Glu Lys Thr Gly Pro Met
                 35                  40                  45
Lys Glu Ile Asn Leu Ala Pro Asp Ser Ser Ser Val Val Val Ser
                 50                  55                  60
Gly Leu Met Val Ala Thr Lys Tyr Glu Val Ser Val Tyr Ala Leu
                 65                  70                  75
Lys Asp Thr Leu Thr Ser Arg Pro Ala Gln Gly Val Val Thr Thr
                 80                  85                  90
Leu Glu Asn Val Ser Pro Pro Arg Arg Ala Arg Val Thr Asp Ala
                 95                 100                 105
Thr Glu Thr Thr Ile Thr Ile Ser Trp Arg Thr Lys Thr Glu Thr
                110                 115                 120
Ile Thr Gly Phe Gln Val Asp Ala Val Pro Ala Asn Gly Gln Thr
                125                 130                 135
Pro Ile Gln Arg Thr Ile Lys Pro Asp Val Arg Ser Tyr Thr Ile
                140                 145                 150
Thr Gly Leu Gln Pro Gly Thr Asp Tyr Lys Ile Tyr Leu Tyr Thr
                155                 160                 165
Leu Asn Asp Asn Ala Arg Ser Ser Pro Val Val Ile Asp Ala Ser
                170                 175                 180
Thr Ala Ile Asp Ala Pro Ser Asn Leu Arg Phe Leu Ala Thr Thr
                185                 190                 195
Pro Asn Ser Leu Leu Val Ser Trp Gln Pro Pro Arg Ala Arg Ile
                200                 205                 210
Thr Gly Tyr Ile Ile Lys Tyr Glu Lys Pro Gly Ser Pro Pro Arg
                215                 220                 225
Glu Val Val Pro Arg Pro Arg Pro Gly Val Thr Glu Ala Thr Ile
                230                 235                 240
Thr Gly Leu Glu Pro Gly Thr Glu Tyr Thr Ile Tyr Val Ile Ala
                245                 250                 255
Leu Lys Asn Asn Gln Lys Ser Glu Pro Leu Ile Gly Arg Lys Lys
                260                 265                 270
Thr Asp Glu Leu Pro Gln Leu Val Thr Leu Pro His Pro Asn Leu
                275                 280                 285
His Gly Pro Glu Ile Leu Asp Val Pro Ser Thr
                290                 295
```

<210> SEQ ID NO 6
<211> LENGTH: 549
<212> TYPE: PRT
<213> ORGANISM: Artificial
<220> FEATURE:
<223> OTHER INFORMATION: Polypeptide having heparin-binding domain and cell-binding domains of fibronectin.

<400> SEQUENCE: 4

```
Pro Thr Asp Leu Arg Phe Thr Asn Ile Gly Pro Asp Thr Met Arg
 1               5                  10                  15

Val Thr Trp Ala Pro Pro Ser Ile Asp Leu Thr Asn Phe Leu
                20                  25                  30

Val Arg Tyr Ser Pro Val Lys Asn Glu Glu Asp Val Ala Glu Leu
                35                  40                  45

Ser Ile Ser Pro Ser Asp Asn Ala Val Val Leu Thr Asn Leu Leu
                50                  55                  60

Pro Gly Thr Glu Tyr Val Val Ser Val Ser Val Tyr Glu Gln
                65                  70                  75

His Glu Ser Thr Pro Leu Arg Gly Arg Gln Lys Thr Gly Leu Asp
                80                  85                  90

Ser Pro Thr Gly Ile Asp Phe Ser Asp Ile Thr Ala Asn Ser Phe
                95                 100                 105

Thr Val His Trp Ile Ala Pro Arg Ala Thr Ile Thr Gly Tyr Arg
               110                 115                 120

Ile Arg His His Pro Glu His Phe Ser Gly Arg Pro Arg Glu Asp
               125                 130                 135

Arg Val Pro His Ser Arg Asn Ser Ile Thr Leu Thr Asn Leu Thr
               140                 145                 150

Pro Gly Thr Glu Tyr Val Val Ser Ile Val Ala Leu Asn Gly Arg
               155                 160                 165

Glu Glu Ser Pro Leu Leu Ile Gly Gln Gln Ser Thr Val Ser Asp
               170                 175                 180

Val Pro Arg Asp Leu Glu Val Val Ala Ala Thr Pro Thr Ser Leu
               185                 190                 195

Leu Ile Ser Trp Asp Ala Pro Ala Val Thr Val Arg Tyr Tyr Arg
               200                 205                 210

Ile Thr Tyr Gly Glu Thr Gly Gly Asn Ser Pro Val Gln Glu Phe
               215                 220                 225

Thr Val Pro Gly Ser Lys Ser Thr Ala Thr Ile Ser Gly Leu Lys
               230                 235                 240

Pro Gly Val Asp Tyr Thr Ile Thr Val Tyr Ala Val Thr Gly Arg
               245                 250                 255

Gly Asp Ser Pro Ala Ser Ser Lys Pro Ile Ser Ile Asn Tyr Arg
               260                 265                 270

Thr Glu Ile Asp Lys Pro Ser Met Ala Ile Pro Ala Pro Thr Asp
               275                 280                 285

Leu Lys Phe Thr Gln Val Thr Pro Thr Ser Leu Ser Ala Gln Trp
               290                 295                 300

Thr Pro Pro Asn Val Gln Leu Thr Gly Tyr Arg Val Arg Val Thr
               305                 310                 315

Pro Lys Glu Lys Thr Gly Pro Met Lys Glu Ile Asn Leu Ala Pro
               320                 325                 330

Asp Ser Ser Ser Val Val Val Ser Gly Leu Met Val Ala Thr Lys
               335                 340                 345

Tyr Glu Val Ser Val Tyr Ala Leu Lys Asp Thr Leu Thr Ser Arg
               350                 355                 360

Pro Ala Gln Gly Val Val Thr Thr Leu Glu Asn Val Ser Pro Pro
               365                 370                 375
```

```
-continued

Arg Arg Ala Arg Val Thr Asp Ala Thr Glu Thr Thr Ile Thr Ile
                380                 385                 390

Ser Trp Arg Thr Lys Thr Glu Thr Ile Thr Gly Phe Gln Val Asp
                395                 400                 405

Ala Val Pro Ala Asn Gly Gln Thr Pro Ile Gln Arg Thr Ile Lys
                410                 415                 420

Pro Asp Val Arg Ser Tyr Thr Ile Thr Gly Leu Gln Pro Gly Thr
                425                 430                 435

Asp Tyr Lys Ile Tyr Leu Tyr Thr Leu Asn Asp Asn Ala Arg Ser
                440                 445                 450

Ser Pro Val Val Ile Asp Ala Ser Thr Ala Ile Asp Ala Pro Ser
                455                 460                 465

Asn Leu Arg Phe Leu Ala Thr Thr Pro Asn Ser Leu Leu Val Ser
                470                 475                 480

Trp Gln Pro Pro Arg Ala Arg Ile Thr Gly Tyr Ile Ile Lys Tyr
                485                 490                 495

Glu Lys Pro Gly Ser Pro Pro Arg Glu Val Val Pro Arg Pro Arg
                500                 505                 510

Pro Gly Val Thr Glu Ala Thr Ile Thr Gly Leu Glu Pro Gly Thr
                515                 520                 525

Glu Tyr Thr Ile Tyr Val Ile Ala Leu Lys Asn Asn Gln Lys Ser
                530                 535                 540

Glu Pro Leu Ile Gly Arg Lys Lys Thr
                545
```

METHOD FOR TRANSFER OF GENE INTO FAT CELL OR PROGENITOR FAT CELL

TECHNICAL FIELD

The present invention relates to a technique for transferring a gene into an adipocyte or a preadipocyte with high efficiency which is useful in the fields of medicine, cell technology, genetic engineering and the like.

BACKGROUND ART

In gene therapy, intractable diseases such as genetic diseases which are due to "errors in genetic information" in cells or cancers are treated or prevented, for example, by providing correct genetic information to repair the functions of the cells, or by adding a new "protective gene" which the cells do not have originally.

A gene used as a therapeutic gene in gene therapy is usually transferred into a tissue or an organ that requires expression of the gene. This case is exemplified by therapy in which CFTR gene is transferred into respiratory epithelial cells in a patient with cystic fibrosis. In another case, a gene may be expressed regardless of tissue or organ. For example, an attempt has been made to transfer a gene encoding factor VII, which is a blood coagulation factor in plasma and is known to be produced in liver, into skeletal myocytes to produce factor VII in the cells for supplying it to plasma (Non-patent Document 1).

If there is no specific restriction concerning the cells in which the gene of interest is to be expressed like in the latter case, one may select a cell to be subjected to gene transfer (a target cell), for example, considering if the cell can be readily handled. For example, attention has been paid to use of adipocytes or preadipocytes as target cells for gene transfer because they can be readily collected, cultured and transplanted into individuals (Patent Document 1).

A method in which a target cell is infected with a retrovirus in the presence of a functional substance that binds to a retrovirus has been developed as a method for infecting a target cell with a retrovirus vector with high efficiency (Patent Documents 2, 3 and 4; Non-patent Document 2). A substance that binds to a target cell or a substance having a target cell-binding site is used in such a method. For an adipocyte or a preadipocyte, no functional substance is known to increase infectivity with a retrovirus.

Patent Document 1: WO 03/106663
Patent Document 2: WO 95/26200
Patent Document 3: WO 97/18318
Patent Document 4: WO 00/01836
Non-patent Document 1: Blood, 101:2963-2972 (2003)
Non-patent Document 2: Nature Medicine, 2:876-882 (1996)

DISCLOSURE OF INVENTION

Problems to be Solved by the Invention

The main object of the present invention is to develop a method for efficiently transferring a foreign gene into an adipocyte or a preadipocyte and to provide a method for producing a transformed cell that is effective in treating or preventing a disease.

Means to Solve the Problems

The present inventors have found that an adipocyte or a preadipocyte is efficiently infected with a retrovirus when the adipocyte or preadipocyte and the retrovirus vector are colocalized using a functional substance having a region of binding to VLA-5 and/or VLA-4. Thus, the present invention has been completed.

The present invention is outlined as follows. The present invention relates to a method for transferring a gene into an adipocyte or a preadipocyte, the method comprising infecting an adipocyte or a preadipocyte with a retrovirus vector having a foreign gene in the presence of a substance having a retrovirus-binding site and a target cell-binding site in a single molecule, or a mixture of a substance having a retrovirus-binding site and another substance having a target cell-binding site, wherein the target cell-binding site contains a region capable of binding to VLA-5 and/or a region capable of binding to VLA-4.

For example, the retrovirus-binding site used according to the present invention may be derived from a substance selected from the group consisting of the heparin-II domain of fibronectin, fibroblast growth factor, the insulin-binding site of type V collagen, polylysine and DEAE-dextran.

A region of binding to VLA-5 and/or VLA-4 derived from fibronectin may be used as the target cell-binding site according to the present invention. The substance having a retrovirus-binding site and a target cell-binding site is exemplified by a polypeptide having the amino acid sequence of SEQ ID NO:1 as well as the amino acid sequence of SEQ ID NO:2 and/or the amino acid sequence of SEQ ID NO:3.

The retrovirus vector used according to the present invention may be a replication-defective retrovirus vector.

Effects of the Invention

According to the present invention, it is possible to efficiently produce an adipocyte or a preadipocyte into which a useful foreign gene is artificially incorporated. Such a cell can be utilized for treatment of various diseases and is medically useful very much.

BEST MODE FOR CARRYING OUT THE INVENTION

The present invention provides a method for increasing efficiency of gene transfer into an adipocyte or a preadipocyte using a retrovirus vector by colocalizing the retrovirus vector and the cell.

A substance having a retrovirus-binding site and an adipocyte or preadipocyte-binding site in a single molecule, or a mixture of a substance having a retrovirus-binding site and another substance having an adipocyte-binding site can be used according to the present invention.

There is no specific limitation concerning the retrovirus-binding site as long as it has an activity of binding to a retrovirus vector. For example, the heparin-II domain of fibronectin, fibroblast growth factor, the insulin-binding site of type V collagen, polylysine, DEAE-dextran or the like can be used. In particular, the polypeptide consisting of the amino acid sequence of SEQ ID NO:1 (H-271) which has a retrovirus-binding site derived from the heparin II domain of fibronectin can be preferably used.

A substance containing a region of binding to VLA-5 and/or VLA-4 can be used as the adipocyte or preadipocyte-biding site. There is also no specific limitation concerning the origin of the region. A known ligand for VLA-5 or VLA-4, or an antibody that recognizes VLA-5 or VLA-4 can be used. A site of binding to VLA-5 or VLA-4 derived from fibronectin can be preferably used. A polypeptide containing the amino acid sequence of SEQ ID NO:2 (C-274) or a polypeptide containing the amino acid sequence of SEQ ID NO:3 (CS-1) exemplifies the above.

A functional substance having both a retrovirus-binding site and an adipocyte or preadipocyte-binding site, or a mixture of a functional substance containing a retrovirus-binding site and another functional substance having an adipocyte or preadipocyte-binding site may be used according to the present invention. In a particularly preferable embodiment, a fibronectin-derived recombinant polypeptide such as the following is used: CH-296 (SEQ ID NO:4) which has all of the amino acid sequences of SEQ ID NOS:1, 2 and 3; H-296 (SEQ ID NO:5) which has the amino acid sequences of SEQ ID NOS:1 and 3; or CH-271 (SEQ ID NO:6) which has the amino acid sequences of SEQ ID NOS:1 and 2. Alternatively, a mixture of H-271 (a polypeptide of the amino acid sequence of SEQ ID NO:1) and C-274 (a polypeptide of the amino acid sequence of SEQ ID NO:2) may be used. CH-296, H-296, CH-271, H-271 and C-274 can be prepared as described in J. Biochem., 110:284-291 (1991) CH-296 is commercially available under the trade name of RetroNectin (registered trademark) from Takara Bio.

There is no specific limitation concerning the method of using the functional substance. For example, the functional substance can be used for coating a surface of a vessel used for infection of a cell with a retrovirus vector. A known method may be used for the coating.

There is no specific limitation concerning the retrovirus vector used according to the present invention. For gene transfer, an artificially modified recombinant retrovirus (i.e., a retrovirus vector) is usually used according to the present invention. Particularly, a replication-defective retrovirus vector is preferable for preventing unlimited infection or gene transfer. Such a vector is made replication-defective so that it cannot autonomously replicate in an infected cell and therefore avirulent. Such a vector can invade a host cell such as a vertebrate cell (particularly a mammalian cell) to stably integrate a foreign gene, which is inserted in the vector, into the chromosomal DNA. Examples of known replication-defective retrovirus vectors include retrovirus vectors (e.g., MFG vector, α-SGC vector (WO 92/07943), pBabe (Nucleic Acids Research, 18:3587-3596 (1990)), pLXIN (Clontech) or pDON-AI (Takara Bio)), lentivirus vectors (human immunodeficiency virus (HIV)-derived vectors, simian immunodeficiency virus (SIV)-derived vectors, etc.) and modifications thereof.

There is no specific limitation concerning the foreign gene carried by the retrovirus vector. Any gene of which the expression in the cell of interest is desired can be inserted. Examples thereof include genes encoding polypeptides (enzymes, hormones, growth factors, cytokines, receptors, structural proteins, etc.), antisense RNAs, ribozymes, decoys, and RNAs that cause RNA interference. If the present invention is to be carried out for gene therapy, a gene encoding a substance that is useful for treatment or prevention of a disease is transferred into a target cell. A gene encoding a polypeptide that exerts its action after it is produced in a cell and then transported outside the cell (e.g., while circulating in blood vessels) such as a secretory enzyme, a hormone, a growth factor or a cytokine is preferable as a gene to be transferred according to the present invention in which an adipocyte or a preadipocyte is used as a target cell.

It is possible according to the present invention to use the foreign gene being inserted into a retrovirus vector under the control of an appropriate promoter (e.g., an LTR promoter in the retrovirus vector or a foreign promoter). Another regulatory element which cooperates with the promoter and a transcription initiation site (e.g., an enhancer sequence) may be present in the vector in order to accomplish transcription of the foreign gene. Preferably, the transferred gene may contain a terminator sequence placed downstream. Furthermore, one may include an appropriate marker gene which enables selection of a cell having a transferred gene (e.g., a drug resistance gene, a gene encoding a fluorescent protein, a gene encoding an enzyme that can function as a reporter such as β-galactosidase or luciferase, a gene encoding a receptor protein).

A retrovirus vector prepared according to a known method may be used according to the present invention. There is no specific limitation concerning the preparation method. A culture supernatant collected from a culture of a retrovirus producer cell suitable for the retrovirus vector to be used can be used according to the present invention. The retrovirus producer cell may be one that stably produces retrovirus particles in the supernatant or one that transiently produces retrovirus particles upon transfection with a retrovirus vector plasmid.

A known packaging cell line such as PG13 (ATCC CRL-10686), PA317 (ATCC CRL-907), GP+E-86 or GP+envAm-12 (U.S. Pat. No. 5,278,056), or Psi-Crip (Proc. Natl. Acad. Sci. USA, 85:6460-6464 (1988)) may be used for preparing a retrovirus producer cell. 293 cell, 293T/17 cell or G3T-hi cell of which the transfection efficiency is high may be used for preparing a retrovirus producer cell.

According to the present invention, it is also possible to use a retrovirus prepared by pseudotyped packaging which has an envelope derived from a virus different from the one from which the genome of the retrovirus vector is derived. For example, a pseudotyped retrovirus having an envelope derived from Moloney murine leukemia virus (MoMLV), gibbon ape leukemia virus (GaLV), vesicular stomatitis virus (VSV) or feline endogenous virus, or a protein that can function as an envelope can be used. Furthermore, one may prepare a retrovirus vector having on its surface a protein that is subjected to sugar chain modification. The retrovirus vector may be prepared using a retrovirus producer cell having a transferred gene for an enzyme involved in glycosylation or the like. Such a retrovirus vector can also be used according to the present invention.

One can use not only a mature adipocyte (a white fat cell, a brown fat cell, etc.) but also a cell that falls within a preadipocyte which is capable of differentiating into an adipocyte as a target cell according to the present invention. Preadipocytes include cells that are capable of directly differentiating into adipocytes, and mesenchymal stem cells or stromal cells which retain abilities to differentiate into various cells including adipocytes. The cell may be a primary culture cell collected from an adipose tissue or the like of a human or a non-human mammal, or an established culture cell line. Examples of sources for collection of adipose tissues include, but are not limited to, subcutaneous fat and visceral fat. An adipose tissue is preferable as a source for collection of a target cell because the risk of dysfunction to the individual due to its collection is low. A mesenchymal stem cell or a stromal cell can be collected from bone marrow or other tissues.

An adipocyte or a preadipocyte having a transferred gene can be efficiently obtained by infecting an adipocyte or a preadipocyte with a retrovirus vector in the presence of the above-mentioned functional substance. If a gene is transferred into a preadipocyte according to the above-mentioned method, an adipocyte having a transferred gene can be obtained by differentiating the resulting cell having a transferred gene into an adipocyte according to a known method.

Alternatively, a preadipocyte having a transferred gene may be transplanted into a living body for differentiating it into an adipocyte.

Although it is not intended to limit the present invention, for example, one can carry out the present invention by infecting a cell with a retrovirus vector in a vessel of which the surface is coated with the above-mentioned functional substance. There is no specific limitation concerning the container as long as it can be used to maintain or culture cells. A Petri dish, a cell culture plate, a flask, a cell culture bag or the like may be used. Immobilization of a functional substance onto the surface of a vessel is carried out using a known procedure suitable for the functional substance to be used. For example, RetroNectin can be used for immobilization being dissolved in sterile distilled water, buffer, saline or the like.

Examples of the methods for infection with a retrovirus vector include, but are not limited to, the following two methods.

(1) An adipocyte or a preadipocyte and a retrovirus vector (e.g., a supernatant of a retrovirus producer cell) are added to a vessel coated with a functional substance and incubated.

(2) A retrovirus vector is added to a vessel coated with a functional substance and incubated, the vessel is washed to remove retrovirus producer cell-derived impurities and the like, and an adipocyte or a preadipocyte is then added thereto and incubated.

The latter is characterized by the ability to remove infection-inhibitory substances which may be present in a retrovirus producer cell, although it is not necessarily required to follow this method. An appropriate infection method may be selected from the above-mentioned methods or other methods according to the vector or the cell to be used.

A cell is cultured with a retrovirus vector during which the medium may be exchanged or an additional vector may be added when necessary. After cultivation, the cell in the vessel is collected and optionally washed. Then, the cell can be used for various purposes. If a preadipocyte is subjected to gene transfer, the cell may be maintained as it is, or it may be subjected to induction of differentiation into a mature cell. For example, a mesenchymal stem cell can be differentiated into a mature adipocyte by cultivation with the addition of an appropriate growth factor or differentiation-inducing substance.

An appropriate cell culture medium can be selected and used for cultivation of a target cell and infection with a retrovirus vector. For example, a commercially available medium or a modification thereof may be used. The medium may contain a growth factor, a cell growth factor or the like as its component.

Optionally, only a cell having a transferred gene may be selected from cells subjected to infection with a retrovirus vector according to the present invention. For example, this procedure can be carried out using expression of a transferred foreign gene (e.g., the above-mentioned marker gene) as an index according to a known method suitable for the characteristic of the gene.

The thus obtained cell having a transferred gene can be transplanted into a human or a non-human mammal to express the transferred gene for exerting the desired action such as an effect of treating or preventing a disease. An adipocyte or a preadipocyte having a transferred gene is usually transplanted into a subcutaneous tissue or an adipose tissue although it is not intended to limit the present invention. Transplantation can be carried out according to a method in which a cell suspension is injected into a site of interest, or a method in which a cell is transplanted at a site of interest that has been surgically incised.

In the above-mentioned embodiment, the donor of the adipocyte or the preadipocyte as a target cell is preferably the same individual as the recipient. However, if the degree of histocompatibility antigen matching is high, an allogenic cell having a transferred gene can be transplanted.

EXAMPLES

The following Examples illustrate the present invention in more detail, but are not to be construed to limit the scope thereof.

Preparation Example 1

Preparation of GFP Expression Retrovirus Vector

A gene encoding red-shift green fluorescent protein (hereinafter referred to as GFP) in a plasmid pQBI25 (Quantum Biotechnologies Inc.) was inserted into a multiple cloning site of a plasmid pDON-AI (Takara Bio, #3650) to construct a plasmid pDON-GFP. A GFP expression retrovirus vector was prepared using Retrovirus Packaging Kit Ampho (Takara Bio, #6161) as well as 293T/17 cell (ATCC CRL-11268) and pDON-GFP according to the protocol attached to the kit. Two preparations of the GFP expression retrovirus vector were prepared by collecting culture supernatants 48 hours (used in Example 1) or 72 hours (used in Example 2) after transfection and used in the subsequent experiments. The collected GFP expression retrovirus vector was stored at −80° C. and rapidly thawed in a water bath at 37° C. before use. 10-, 40- and 160-fold dilutions of the supernatant with Preadipocyte Growth Medium (hereinafter referred to as PGM medium, prepared using Cambrex, #B8000) were used in the test as described in Example 1, and 4-, 16- and 64-fold dilutions of the supernatant with Dulbecco's modified Eagle medium (Sigma, #D6046) (hereinafter referred to as DMEM medium) containing 10% fetal bovine serum (FBS, Cambrex) were used in the test as described in Example 2.

Example 1

Gene Transfer into Human Preadipocyte Using RetroNectin (1) Immobilization of RetroNectin onto Culture Plate 500 µl of a solution of RetroNectin (registered trademark, Takara Bio, #T100A) in phosphate-buffered saline (PBS) at a concentration of 20 µg/ml was added to each well of a non-treatment 24-well culture plate (Becton-Dickinson, #351147). Immobilization was carried out at 4° C. overnight. The solution was then removed from each well, 500 µl of PBS containing 2% bovine serum albumin was added to each well and the plate was left at room temperature for 30 minutes or more. The prepared RetroNectin-immobilized culture plate was subjected to an experiment after washing once with PBS.

(2) Gene Transfer According to RetroNectin Binding Method

500 µl of the GFP expression retrovirus vector dilution prepared in Preparation Example 1 was added to each well of the RetroNectin-immobilized culture plate prepared in (1), and the plate was incubated in a $CO_2$ incubator at 32° C. for 6 hours. The supernatant was then removed from each well, the well was washed once with PBS, 500 µl of a suspension of human preadipocytes (Cambrex, #PT5020) in PGM medium at a density of $4 \times 10^4$ cells/ml was seeded into the well, and the cells were cultured in a $CO_2$ incubator at 37° C. for 4 days.

After cultivation, the cells were subjected to flow cytometry analysis. All experiments were carried out in duplicate.

(3) Gene Transfer According to RetroNectin SN Method

500 μl of a suspension of human preadipocytes in PGM medium at a density of $4 \times 10^4$ cells/ml was placed in a tube, the tube was centrifuged at 1,500×g for 5 minutes at room temperature, and the supernatant was removed. 500 μl of the GFP expression retrovirus vector dilution prepared in Preparation Example 1 was added to the tube and the precipitated cells were suspended. The suspension was added to each well of the RetroNectin-immobilized culture plate prepared in (1), and the cells were cultured in a $CO_2$ incubator at 37° C. for 4 days. After cultivation, the cells were subjected to flow cytometry analysis. All experiments were carried out in duplicate.

(4) Gene Transfer According to Polybrene SN Method

As a control, gene transfer was carried out according to a polybrene SN method in which RetroNectin was not used. 500 μl of a suspension of human preadipocytes in PGM medium at a density of $4 \times 10^4$ cells/ml was seeded into each well of a 24-well culture plate (Becton-Dickinson, #353047), and the cells were cultured in a $CO_2$ incubator at 37° C. overnight. The culture supernatant was then removed, 500 μl of the GFP expression retrovirus vector dilution prepared in Preparation Example 1 to which polybrene (hexadimethrine bromide, Aldrich, #10768-9) aqueous solution was added to result in a final concentration of 8 μg/ml was added to each well, and the cells were cultured in a $CO_2$ incubator at 37° C. overnight. The culture supernatant was removed, 500 μl of fresh PGM medium was added to each well, the cultivation was further continued for 3 days, and the cells were subjected to flow cytometry analysis. All experiments were carried out in duplicate.

(5) Measurement of Gene Transfer Efficiency

The ratios of GFP-expressing cells were measured by flow cytometry (Cytomics FC500, Beckman Coulter) for the cells subjected to gene transfer according to the methods of (2), (3) and (4) to assess the gene transfer efficiencies. Specifically, the cultured cells were detached from the culture plate using a trypsin-EDTA solution (Gibco-BRL, #25200-056), suspended in PGM medium, and subjected to flow cytometry analysis. The results are shown in Table 1. Table 1 shows gene transfer efficiencies (ratios of GFP-expressing cells) (%) observed upon gene transfer using the 10-, 40- or 160-fold dilution of the GFP expression retrovirus vector according to the respective methods.

TABLE 1

|  | 10-fold dilution | 40-fold dilution | 160-fold dilution |
| --- | --- | --- | --- |
| RetroNectin binding method | 73.15 | 63.96 | 34.26 |
| RetroNectin SN method | 82.09 | 70.98 | 43.31 |
| Polybrene SN method | 55.51 | 45.63 | 22.33 |

As shown in Table 1, gene transfer efficiencies higher than that observed for the polybrene SN method as a control were observed for the RetroNectin binding method and the RetroNectin SN method. Thus, the usefulness of RetroNectin for gene transfer into adipocytes was shown.

Example 2

Gene Transfer into Mouse Preadipocyte Using RetroNectin (1) Immobilization of RetroNectin onto Culture Plate Immobilization was carried out as described in Example 1-(1).

(2) Gene Transfer According to RetroNectin Binding Method

500 μl of the GFP expression retrovirus vector dilution prepared in Preparation Example 1 was added to each well of the RetroNectin-immobilized culture plate prepared in (1), and the late was incubated in a $CO_2$ incubator at 32° C. for 6 hours. The supernatant was then removed from each well, the well was washed once with PBS, 500 μl of a suspension of cells of mouse preadipocyte cell line 3T3-L1 (ATCC CCL-92.1) in DMEM medium at a density of $4 \times 10^4$ cells/ml was seeded into the well, and the cells were cultured in a $CO_2$ incubator at 37° C. for 1 day. The culture supernatant was removed, 500 μl of fresh DMEM medium was added to each well, the cultivation was further continued in a $CO_2$ incubator at 37° C. for 3 days, and the cells were subjected to flow cytometry analysis. All experiments were carried out in duplicate.

(3) Gene Transfer According to RetroNectin SN Method

500 μl of a suspension of 3T3-L1 cells in PGM medium at a density of $4 \times 10^4$ cells/ml was placed in a tube, the tube was centrifuged at 1,500×g for 5 minutes at room temperature, and the supernatant was removed. 500 μl of the GFP expression retrovirus vector dilution prepared in Preparation Example 1 was added to the tube and the precipitated cells were suspended. The suspension was added to each well of the RetroNectin-immobilized culture plate prepared in (1), and the cells were cultured in a $CO_2$ incubator at 37° C. for 1 day. The culture supernatant was removed, 500 μl of fresh DMEM medium was added to each well, the cultivation was further continued in a $CO_2$ incubator at 37° C. for 3 days, and the cells were subjected to flow cytometry analysis. All experiments were carried out in duplicate.

(4) Gene Transfer According to Polybrene SN Method

As a control, gene transfer was carried out according to a polybrene SN method in which RetroNectin was not used. Gene transfer was carried out as described in Example 1-(4) except that 3T3-L1 cell was used as a cell and DMEM medium was used as a medium.

(5) Measurement of Gene Transfer Efficiency

The ratios of GFP-expressing cells were measured by flow cytometry for the cells subjected to gene transfer according to the methods of (2), (3) and (4) to assess the gene transfer efficiencies. Specifically, the cultured cells were detached from the culture plate using a trypsin-EDTA solution, suspended in DMEM medium, and subjected to flow cytometry analysis. The results are shown in Table 2. Table 2 shows gene transfer efficiencies (ratios of GFP-expressing cells) (%) observed upon gene transfer using the 4-, 16- or 64-fold dilution of the GFP expression retrovirus vector according to the respective methods.

TABLE 2

|  | 4-fold dilution | 16-fold dilution | 64-fold dilution |
| --- | --- | --- | --- |
| RetroNectin binding method | 71.68 | 49.79 | 17.33 |
| RetroNectin SN method | 54.07 | 45.74 | 21.86 |
| Polybrene SN method | 16.60 | 23.05 | 12.51 |

As shown in Table 2, gene transfer efficiencies higher than that observed for the polybrene SN method as a control were observed for the RetroNectin binding method or the RetroNectin SN method. Thus, the usefulness of RetroNectin was shown.

Preparation Example 2

Preparation of GFP Expression Retrovirus Vector Using Different Producer Cell

A GFP expression retrovirus vector was prepared according to the method as described in Preparation Example 1. In addition to 293T/17 cell, G3T-hi cell (Takara Bio, #6163) was also used as a producer cell. Two preparations of the GFP expression retrovirus vector were prepared by collecting culture supernatants 48 hours or 72 hours after transfection, and stored by freezing at −80° C.

Example 3

Differentiation Induction of Cell Having Transferred Gene (1) Preculture of Cell Purchased human preadipocytes derived from subcutaneous fat (Cambrex, #PT5020) were thawed, cultured for about 48 hours using PGM medium and a 225-cm$^2$ flask (Corning, #431082) to increase the cell number, suspended in a storage solution consisting of 90% FBS/10% DMSO (Sigma), and stored in liquid nitrogen.

Upon gene transfer, the stored human preadipocytes were rapidly thawed in a water bath at 37° C., washed with PGM medium, seeded into a 175-cm$^2$ flask (Becton-Dickinson, #353028) at about 4000 cells/0.2 ml/cm$^2$, and cultured for about 48 hours. The cultured cells were collected using a trypsin-EDTA solution. A portion was used for an experiment according to the polybrene method as described in (6) below. The remainder was seeded into a 175-cm$^2$ flask, further cultured for about 24 hours, and then subjected to experiments according to the RetroNectin methods as described in (4) and (5) below.

(2) Immobilization of RetroNectin onto Culture Plate

Immobilization was carried out as described in Example 1-(1) except that a nontreatment 48-well culture plate (Becton-Dickinson, #351178) was used as a plate, and the volume of the RetroNectin solution added to the well was 200 µl.

(3) Preparation of Virus Vector Supernatant

The GFP expression retrovirus vector prepared in Preparation Example 2 (producer cell: 293T/17 cell; collected 48 hours after transfection) was rapidly thawed in a water bath at 37° C., diluted 10- or 40-fold with PGM medium, and subjected to experiments.

(4) Gene Transfer According to RetroNectin Binding Method

200 µl of the GFP expression retrovirus vector dilution prepared in (3) was added to each well of the RetroNectin-immobilized culture plate prepared in (2), and the plate was incubated in a CO$_2$ incubator at 32° C. for 5 hours. The supernatant was then removed from each well, the well was washed once with a phosphate buffer aqueous solution, 200 µl of a suspension of human preadipocytes precultured in (1) in PGM medium at a density of 4×10$^4$ cells/ml was seeded into the well, and the cells were cultured in a CO$_2$ incubator at 37° C. for 4 days. After cultivation, the cells were subjected to flow cytometry analysis. All experiments were carried out in duplicate.

(5) Gene Transfer According to RetroNectin SN Method

200 µl of a suspension of human preadipocytes precultured in (1) in PGM medium at a density of 4×10$^4$ cells/ml was placed in a tube, the tube was centrifuged at about 1,800×g for 5 minutes at room temperature, and the supernatant was removed. 200 µl of the GFP expression retrovirus vector dilution prepared in (3) was added to the tube and the precipitated cells were suspended. The suspension was added to each well of the RetroNectin-immobilized culture plate prepared in (2), and the cells were cultured in a CO$_2$ incubator at 37° C. for 4 days. After cultivation, the cells were subjected to flow cytometry analysis. All experiments were carried out in duplicate.

(6) Gene Transfer According to Polybrene SN Method

As a control, gene transfer was carried out according to a polybrene SN method in which RetroNectin was not used. 200 µl of a suspension of human preadipocytes precultured in (1) in PGM medium at a density of 4×10$^4$ cells/ml was seeded into each well of a 48-well cell culture plate (Becton-Dickinson, #353078), and the cells were cultured in a CO$_2$ incubator at 37° C. overnight. The culture supernatant was then removed, 200 µl of the GFP expression retrovirus vector dilution prepared in (3) to which polybrene aqueous solution was added to result in a final concentration of 8 µg/ml was added to each well, and the cells were cultured in a CO$_2$ incubator at 37° C. for 24 hours. The culture supernatant was removed, 200 µl of fresh PGM medium was added to each well, the cultivation was further continued for 3 days, and the cells were subjected to flow cytometry analysis. All experiments were carried out in duplicate.

(7) Measurement of Gene Transfer Efficiency

The ratios of GFP-expressing cells were measured according to the method as described in Example 1-(5) by flow cytometry for the cells subjected to gene transfer according to the methods of (4), (5) and (6). The results are shown in Table 3. Table 3 shows gene transfer efficiencies (ratios of GFP-expressing cells) (%) observed upon gene transfer using the 10- or 40-fold dilution of the GFP expression retrovirus vector according to the respective methods.

TABLE 3

|  | 10-fold dilution | 40-fold dilution |
| --- | --- | --- |
| RetroNectin binding method | 45.17 | 40.55 |
| RetroNectin SN method | 42.66 | 38.68 |
| Polybrene SN method | 38.82 | 38.23 |

As shown in Table 3, gene transfer efficiencies higher than that observed for the polybrene SN method as a control were observed for the RetroNectin binding method or the RetroNectin SN method. Thus, the usefulness of RetroNectin for gene transfer into adipocytes was shown.

(8) Induction of Differentiation of Cells Having Transferred Gene and Measurement of Gene Transfer Efficiency in Differentiated Adipocytes For determining if human preadipocytes subjected to gene transfer maintained their ability to differentiate into adipocytes, differentiation of cells subjected to gene transfer were induced. Differentiation of the cells subjected to gene transfer according to the methods of (4), (5) and (6) were induced as follows. After a culture supernatant was removed, 250 µl of Adipocyte Differentiation Medium (hereinafter referred to as ADM medium, prepared using Preadipocyte Growth Medium Bullet Kit, Cambrex, #PT8000) was added to each well, an equal volume (250 µl) of PGM medium was further added to the well and mixed, and the cultivation was carried out for 7 days. After differentiation induction, the adipocytes were subjected to flow cytometry analysis as described in (7). The results are shown in Table 4. Table 4 shows ratios of GFP-expressing cells (%) observed for cells subjected to differentiation into adipocytes by the differentiation induction following gene transfer using the 10- or 40-fold dilution of the GFP expression retrovirus vector according to the respective methods.

TABLE 4

|  | 10-fold dilution | 40-fold dilution |
| --- | --- | --- |
| RetroNectin binding method | 47.60 | 40.09 |
| RetroNectin SN method | 45.44 | 37.96 |
| Polybrene SN method | 35.92 | 34.65 |

As shown in Table 4, when the ratios of GFP-expressing cells were compared with the values of gene transfer efficiency as shown in Table 3, almost no difference was observed for the cells subjected to gene transfer according to the respective methods. Thus, it was confirmed that the gene transferred into preadipocytes was stably maintained after differentiation into adipocytes.

(9) Assessment of Ability to Differentiate into Adipocyte by Measurement of Accumulated Triglyceride Amount The differentiating ability of cells subjected to gene transfer followed by differentiation induction was assessed by measuring the accumulated triglyceride amount in the cells. Differentiation of the cells subjected to gene transfer according to the methods of (4), (5) and (6) as well as control cells subjected to gene transfer using a medium without a virus were induced as described in (8). After removing a culture supernatant, the cells were washed twice with a phosphate buffer aqueous solution, and 250 μl a 2:3 mixture of isopropanol and hexane was added to each well. After leaving at room temperature for 30 minutes, a supernatant was collected. The process of addition of a mixture of isopropanol and hexane, leaving and collection was repeated in a similar manner. The solvent was removed from the collected mixture by concentration/drying, and the resulting triglyceride was dissolved in dimethylformamide (Wake Pure Chemical Industries, #047-25475). The thus obtained sample was reacted using Triglyceride E-Test Wako (Wako Pure Chemical Industries, #432-40201), and the absorbance at 570 nm was then measured using an absorbance plate reader (Micro-Reader 4, Hyperion) to calculate the triglyceride content of the sample.

Protein was collected from the cells after triglyceride collection by adding 250 μl of 1 N sodium hydroxide solution (prepared using Nacalai Tesque, #31511-05) to each well and leaving at room temperature for 30 minutes. The concentration of the collected protein was determined using Micro BCA Protein Assay Reagent Kit (Pierce, 23235). The accumulated triglyceride amount of the sample was corrected by dividing the value by the protein amount to determine the triglyceride amount per unit protein amount. The results are shown in Table 5. Table 5 shows accumulated triglyceride amounts (indicated with "TG" in μg), protein amounts (indicated with "protein" in μg) and triglyceride amounts per unit protein amounts (indicate with "TG/protein" in μg) observed for cells subjected to differentiation induction following gene transfer using PGM medium without a virus (mock), or the 10- or 40-fold dilution of the GFP expression retrovirus vector supernatant according to the respective methods.

TABLE 5

| Transfer method | | mock | 10-fold dilution | 40-fold dilution |
| --- | --- | --- | --- | --- |
| RetroNectin binding method | TG | 31.39 | 30.50 | 24.54 |
|  | protein | 73.57 | 66.08 | 65.81 |
|  | TG/protein | 0.43 | 0.46 | 0.37 |
| RetroNectin SN method | TG | 27.67 | 25.51 | 27.82 |
|  | protein | 67.26 | 64.74 | 65.97 |
|  | TG/protein | 0.41 | 0.39 | 0.42 |
| Polybrene SN method | TG | 30.12 | 31.46 | 31.61 |
|  | protein | 68.60 | 69.29 | 84.23 |
|  | TG/protein | 0.45 | 0.46 | 0.38 |

As shown in Table 5, accumulation of triglyceride was observed for cells subjected to gene transfer followed by differentiation induction according to each method. No significant difference was observed between the mock cells and the cells subjected to gene transfer using RetroNectin. An equivalent TG/protein value was observed for the cells obtained by differentiation induction of human preadipocytes not subjected to gene transfer in a similar manner. Thus, it was shown that the differentiating ability of preadipocytes was not reduced by gene transfer.

Example 4

Gene Transfer Using Virus Vector Prepared Using Different Producer Cell (1) Preculture of Cell
Preculture was carried out as described in Example 3-(1).
(2) Immobilization of RetroNectin onto Culture Plate
Immobilization was carried out as described in Example 3-(2).
(3) Preparation of Virus Vector Supernatant
The GFP expression retrovirus vector prepared in Preparation Example 2 was rapidly thawed in a water bath at 37° C., diluted 10-, 40- or 160-fold with PGM medium, and subjected to experiments. Culture supernatants collected from transfected 293T/17 cell or G3T-hi cell after cultivation for 72 hours were subjected to experiments as GFP expression retrovirus vectors.
(4) Gene Transfer According to RetroNectin Binding Method
Gene transfer was carried out as described in Example 3-(4).
(5) Gene Transfer According to RetroNectin SN Method
Gene transfer was carried out as described in Example 3-(5).
(6) Measurement of Gene Transfer Efficiency
Measurement was carried out as described in Example 3-(7). The results are shown in Table 6. Table 6 shows gene transfer efficiencies (ratios of GFP-expressing cells) (%) observed upon gene transfer using the 10-, 40-, or 160-fold dilution of the GFP expression retrovirus vector according to the respective methods.

TABLE 6

| Transfer method | Producer cell | 10-fold dilution | 40-fold dilution | 160-fold dilution |
| --- | --- | --- | --- | --- |
| Retronectin binding method | 293T/17 | 44.01 | 34.16 | 13.02 |
|  | G3T-hi | 51.13 | 45.96 | 28.78 |
| Retronectin SN method | 293T/17 | 36.99 | 26.01 | 11.81 |
|  | G3T-hi | 55.28 | 52.95 | 34.45 |

As shown in Table 6, it was shown that it was possible to transfer a gene according to the RetroNectin method also using a virus vector prepared using G3T-hi cell.

Example 5

Gene Transfer Using PGM Medium Containing Human Serum (1) Preculture of Cell

Preculture was carried out as described in Example 3-(1) except that a 75-cm$^2$ flask (Becton-Dickinson, #353110) was used for preculture and the cells were seeded at about 9000 cells/0.2 ml/cm$^2$.

(2) Immobilization of RetroNectin onto Culture Plate

Immobilization was carried out as described in Example 3-(2).

(3) Preparation of Virus Vector Supernatant

The GFP expression retrovirus vector prepared in Preparation Example 2 (producer cell: 293T/17 cell; collected 72 hours after transfection) was rapidly thawed in a water bath at 37° C., diluted 10-, 40- or 160-fold with PGM medium containing 10% human AB serum (Cambrex) in place of 10% FBS (hereinafter referred to as 10HPGM medium), and subjected to experiments.

(4) Gene Transfer According to RetroNectin Binding Method

Gene transfer was carried out as described in Example 3-(4) except that 10HPGM medium was used as a medium.

(5) Gene Transfer According to RetroNectin SN Method

Gene transfer was carried out as described in Example 3-(5) except that 10HPGM medium was used as a medium.

(6) Gene Transfer According to Polybrene SN Method

Gene transfer was carried out as described in Example 3-(6) except that 10HPGM medium was used as a medium.

(7) Measurement of Gene Transfer Efficiency

Measurement was carried out as described in Example 3-(7) The results are shown in Table 7. Table 7 shows gene transfer efficiencies (ratios of GFP-expressing cells) (%) observed upon gene transfer using the 1-, 40-, or 160-fold dilution of the GFP expression retrovirus vector with 10HPGM medium according to the respective methods.

TABLE 7

| | 10-fold dilution | 40-fold dilution | 160-fold dilution |
|---|---|---|---|
| RetroNectin binding method | 23.30 | 21.58 | 12.99 |
| RetroNectin SN method | 34.45 | 25.88 | 18.38 |
| Polybrene SN method | 11.45 | 9.08 | 3.27 |

As shown in Table 7, it was shown that it was also possible to transfer a gene using a medium containing human serum. The transfer efficiency observed for the RetroNectin method was higher than that observed for the polybrene method also when the medium containing human serum was used for gene transfer. Thus, the usefulness of RetroNectin was shown.

Example 6

Gene Transfer into Human Preadipocyte Precultured Under Different Conditions (1) Preculture of Cell Preculture was carried out as described in Example 3-(1) except the following. Upon preculture, cells were seeded under three types of conditions, i.e., into a 12.5-cm$^2$ flask (Becton-Dickinson, #353107) at about 13000 cells/0.2 ml/cm$^2$, into a 25-cm$^2$ flask (Becton-Dickinson, #353108) at about 6600 cells/0.2 ml/cm$^2$, or into a 75-cm$^2$ flask at about 2200 cells/0.2 ml/cm$^2$. For the respective three types of conditions, the following two preparations were prepared and used for gene transfer: the cells were cultured for about 72 hours; or the cells were collected by detaching after culturing for about 48 hours, and portions thereof were seeded into flasks of the same area at almost the same cell densities and cultured for about 24 hours.

(2) Immobilization of RetroNectin onto Culture Plate

Immobilization was carried out as described in Example 3-(2).

(3) Preparation of Virus Vector Supernatant

The GFP expression retrovirus vector prepared in Preparation Example 2 (producer cell: G3T-hi cell; collected 72 hours after transfection) was rapidly thawed in a water bath at 37° C., diluted 10-, 40- or 160-fold with PGM medium, and subjected to experiments.

(4) Gene Transfer According to RetroNectin SN Method

Gene transfer was carried out as described in Example 3-(5).

(5) Measurement of Gene Transfer Efficiency

Measurement was carried out as described in Example 3-(7). The results are shown in Table 8. Table 8 shows gene transfer efficiencies (ratios of GFP-expressing cells) (%) observed upon gene transfer into cells precultured under different conditions using the 10-, 40-, or 160-fold dilution of the GFP expression retrovirus vector according to the RetroNectin SN methods.

TABLE 8

| Preculture conditions | Cell density | 10-fold dilution | 40-fold dilution | 160-fold dilution |
|---|---|---|---|---|
| Cultured for 72 hours | 13000 cells/mL | 13.05 | 10.03 | 4.70 |
| | 6600 cells/mL | 13.83 | 8.66 | 5.32 |
| | 2200 cells/mL | 29.70 | 28.72 | 16.02 |
| Passaged after 48 hours | 13000 cells/mL | 27.88 | 20.16 | 10.54 |
| | 6600 cells/mL | 38.83 | 34.28 | 19.06 |
| | 2200 cells/mL | 45.81 | 42.26 | 24.57 |

As shown in Table 8, it was shown that transfer efficiencies varied depending on the preculture conditions. It was shown that the transfer efficiency according to the RetroNectin method could be further increased by optimizing the conditions for culture or passage of cells.

Example 7

Gene Transfer into Human Preadipocyte Derived from Visceral Fat (1) Preculture of Cell Purchased human preadipocytes derived from visceral fat (Cambrex, #PT5005) were thawed, cultured for about 48 hours using PGM medium and a 225-cm$^2$ flask to increase the cell number, suspended in a storage solution consisting of 90% FBS (Cambrex)/10% DMSO (Sigma), and stored in liquid nitrogen.

Upon gene transfer, the stored preadipocytes were rapidly thawed in a water bath at 37° C., washed with PGM medium, seeded into a 75-cm$^2$ flask at about 3700 cells/0.2 ml/cm$^2$, and cultured for about 48 hours. The cultured cells were collected using a trypsin-EDTA solution. A portion was used for an experiment according to the polybrene method as described in (6) below. The remainder was seeded into a 75-cm$^2$ flask, further cultured for about 24 hours, and then subjected to experiments according to the RetroNectin methods as described in (4) and (5) below.

(2) Immobilization of RetroNectin onto Culture Plate

Immobilization was carried out as described in Example 3-(2).

(3) Preparation of Virus Vector Supernatant

The GFP expression retrovirus vector prepared in Preparation Example 2 (producer cell: 293T/17 cell; collected 48 hours after transfection) was rapidly thawed in a water bath at 37° C., diluted 10- or 40-fold with PGM medium, and subjected to experiments.

(4) Gene Transfer According to RetroNectin Binding Method

Gene transfer was carried out as described in Example 3-(4) except that human preadipocytes derived from visceral fat as described in (1) above were used as cells.

(5) Gene Transfer According to RetroNectin SN Method

Gene transfer was carried out as described in Example 3-(5) except that human preadipocytes derived from visceral fat as described in (1) above were used as cells.

(6) Gene Transfer According to Polybrene SN Method

Gene transfer was carried out as described in Example 3-(6) except that human preadipocytes derived from visceral fat as described in (1) above were used as cells.

(7) Measurement of Gene Transfer Efficiency

Measurement was carried out as described in Example 3-(7). The results are shown in Table 9. The table shows gene transfer efficiencies (ratios of GFP-expressing cells) (%) observed upon gene transfer using the 10- or 40-fold dilution of the GFP expression retrovirus vector according to the respective methods.

TABLE 9

|  | 10-fold dilution | 40-fold dilution |
|---|---|---|
| RetroNectin binding method | 61.19 | 53.27 |
| RetroNectin SN method | 65.47 | 59.57 |
| Polybrene SN method | 28.66 | 25.98 |

As shown in Table 9, it was shown that human preadipocytes derived from visceral fat could be used for gene transfer like the subcutaneous fat-derived cells. In addition, gene transfer efficiencies higher than that observed for the polybrene SN method as a control were observed for the RetroNectin binding method and the RetroNectin SN method. Thus, the usefulness of RetroNectin was shown.

Preparation Example 3

Preparation of ZsGreen Expression Retrovirus Vector

A gene encoding a fluorescent protein ZsGreen in a plasmid pZsGreen1-N1 (Clontech Laboratories, #632448) was inserted into a multiple cloning site of a plasmid pDON-AI to construct a plasmid pDON-ZsGreen. A ZsGreen expression retrovirus vector was prepared using pDON-ZsGreen according to the method as described in Preparation Example 1. The collected ZsGreen expression retrovirus vector was stored at −80° C. and rapidly thawed in a water bath at 37° C. before use. 10- and 100-fold dilutions of the supernatant with PGM medium were subjected to experiments.

Example 8

Gene Transfer Using CH-271

(1) Preculture of Cell

Human preadipocytes derived from subcutaneous fat were precultured as described in Example 3-(1) and used for the subsequent experiments.

(2) Immobilization of CH-271 onto Culture Plate

Immobilization was carried out as described in Example 3-(2) except that CH-271 was immobilized in place of RetroNectin. The concentration of CH-271 in the solution used for immobilization was 77 μg/ml.

(3) Gene Transfer According to CH-271 Binding Method

Gene transfer was carried out as described in Example 3-(4) using the ZsGreen expression retrovirus vector supernatant prepared in Preparation Example 3 and the CH-271-immobilized culture plate prepared in (2).

(4) Gene Transfer According to CH-271 SN Method

Gene transfer was carried out as described in Example 3-(5) using the ZsGreen expression retrovirus vector supernatant prepared in Preparation Example 3 and the CH-271-immobilized culture plate prepared in (2).

(5) Gene Transfer According to Protamine SN Method

As a control, gene transfer was carried out according to a protamine SN method in which a polypeptide such as RetroNectin or CH-271 was not used. 200 μl of a suspension of human preadipocytes precultured in (1) in PGM medium at a density of $4 \times 10^4$ cells/ml was seeded into each well of a 48-well cell culture plate, and the cells were cultured in a $CO_2$ incubator at 37° C. overnight. The culture supernatant was then removed, 200 μl of the ZsGreen expression retrovirus vector supernatant prepared in Preparation Example 3 to which Novo protamine sulfate (Mochida Pharmaceutical) was added to result in a final concentration of 4 μg/ml was added to each well, and the cells were cultured in a $CO_2$ incubator at 37° C. for 24 hours. The culture supernatant was removed, 200 μl of fresh PGM medium was added to each well, the cultivation was further continued for 3 days, and the cells were subjected to flow cytometry analysis. All experiments were carried out in duplicate.

(6) Measurement of Gene Transfer Efficiency

The ratios of ZsGreen-expressing cells were measured according to the method as described in Example 1-(5) for the cells subjected to gene transfer according to the methods of (3), (4) and (5). The results are shown in Table 10. Table 10 shows gene transfer efficiencies (ratios of ZsGreen-expressing cells) (%) observed upon gene transfer using the 10- or 100-fold dilution of the ZsGreen expression retrovirus vector supernatant with PGM medium according to the respective methods.

TABLE 10

|  | 10-fold dilution | 100-fold dilution |
|---|---|---|
| CH-271 binding method | 62.47 | 34.37 |
| CH-271 SN method | 60.24 | 43.54 |
| Protamine SN method | 31.52 | 16.80 |

As shown in Table 10, it was shown that CH-271 could be used to transfer a gene into human preadipocytes like RetroNectin. CH-271 is composed of a retrovirus-binding site derived from fibronectin and a region capable of binding to VLA-5. Gene transfer efficiencies higher than that observed for the protamine method as a control were observed for the CH-271 binding method and the CH-271 SN method. Thus, the effectiveness of the transfer method in which the target cells and the retrovirus vector were colocalized using CH-271 was shown.

Example 9

Gene Transfer Using H-296

(1) Preculture of Cell

Human preadipocytes derived from subcutaneous fat were precultured as described in Example 3-(1) except that Preadipocyte Growth Medium-2 (hereinafter referred to as PGM-2 medium, prepared using Cambrex, #PT-8002) was used as a medium.

(2) Immobilization of H-296 onto Culture Plate

Immobilization was carried out as described in Example 3-(2) except that H-296 was immobilized in place of RetroNectin. The concentration of H-296 in the solution used for immobilization was 100 μg/ml.

(3) Gene Transfer According to H-296 Binding Method

Gene transfer was carried out as described in Example 3-(4) using the ZsGreen expression retrovirus vector supernatant prepared in Preparation Example 3 and the H-296-immobilized culture plate prepared in (2). PGM-2 medium was used as a medium.

(4) Gene Transfer According to H-296 SN Method

Gene transfer was carried out as described in Example 3-(5) using the ZsGreen expression retrovirus vector supernatant prepared in Preparation Example 3 and the H-296-immobilized culture plate prepared in (2). PGM-2 medium was used as a medium.

(5) Gene Transfer According to Protamine SN Method

Gene transfer was carried out as described in Example 8-(5) except that PGM-2 medium was used as a medium.

(6) Measurement of Gene Transfer Efficiency

The ratios of ZsGreen-expressing cells were measured according to the method as described in Example 1-(5) for the cells subjected to gene transfer according to the methods of (3), (4) and (5). The results are shown in Table 11. Table 11 shows gene transfer efficiencies (ratios of ZsGreen-expressing cells) (%) observed upon gene transfer using the 10- or 100-fold dilution of the ZsGreen expression retrovirus vector supernatant with PGM-2 medium according to the respective methods.

TABLE 11

|  | 10-fold dilution | 100-fold dilution |
| --- | --- | --- |
| H-296 binding method | 28.57 | 9.20 |
| H-296 SN method | 32.49 | 10.97 |
| Protamine SN method | 16.68 | 6.33 |

As shown in Table 11, it was shown that H-296 could be used to transfer a gene into human preadipocytes like RetroNectin. H-296 is composed of a retrovirus-binding site derived from fibronectin and a region capable of binding to VLA-4. Gene transfer efficiencies higher than that observed for the protamine method as a control were observed for the H-296 binding method and the H-296 SN method. Thus, the effectiveness of the transfer method in which the target cells and the retrovirus vector were colocalized using H-296 was shown.

INDUSTRIAL APPLICABILITY

According to the present invention, it is possible to transfer a useful gene into an adipocyte or a preadipocyte with high efficiency. The cell having a transferred gene can express a gene product that is useful for treatment or prevention of a disease in a biological individual. Thus, the present invention provides a method of gene therapy by transplanting such a cell.

Sequence Listing Free Text

SEQ ID NO:4: Polypeptide having cell-binding domain and heparin-binding domains of fibronectin.

SEQ ID NO:6: Polypeptide having cell-binding domain and heparin-binding domains of fibronectin.

The invention claimed is:

1. A method for increasing the efficiency transferring a gene into an adipocyte or a preadipocyte, the method comprising infecting an adipocyte or a preadipocyte with the proviso that the preadipocyte is a cell that is capable of directly differentiating into an adipocyte and is not a mesenchymal stem cell or stromal cell which retains abilities to differentiate into various cell types with a retrovirus vector having a foreign gene in the presence of a polypeptide having the amino acid sequence of:
   (a) SEQ ID NO:1 and SEQ ID NO:2;
   (b) SEQ ID NO:1 and SEQ ID NO:3; or
   (c) SEQ ID NO:1 and SEQ ID NO:2 and SEQ ID NO:3.

2. The method according to claim 1, wherein the retrovirus vector is a replication-defective retrovirus vector.

3. In a method for transferring a gene into an adipocyte or a preadipocyte, the improvement comprising infecting an adipocyte or a preadipocyte with the proviso that the preadipocyte is a cell that is capable of directly differentiating into an adipocyte and is not a mesenchymal stem cell or stromal cell which retains abilities to differentiate into various cell types with a retrovirus vector having a foreign gene in the presence of a polypeptide having the amino acid sequence of:
   (a) SEQ ID NO:1 and SEQ ID NO:2;
   (b) SEQ ID NO:1 and SEQ ID NO:3; or
   (c) SEQ ID NO:1 and SEQ ID NO:2 and SEQ ID NO:3.

4. The method according to claim 3 wherein the retrovirus vector is a replication-defective retrovirus vector.

\* \* \* \* \*